US00PP15010P2

(12) United States Plant Patent
Pieters

(10) Patent No.: US PP15,010 P2
(45) Date of Patent: Jul. 13, 2004

(54) CHRYSANTHEMUM PLANT NAMED 'GEDI TWO YLBUR'

(50) Latin Name: *Chrysanthemum morifolium*
Varietal Denomination: Gedi Two Ylbur

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/613,321

(22) Filed: Jul. 3, 2003

(51) Int. Cl.[7] ..... A01H 5/00
(52) U.S. Cl. ..... Plt./295
(58) Field of Search ..... Plt./295, 286

(56) References Cited

U.S. PATENT DOCUMENTS

PP10,215 P 1/1998 Pieters ..... Plt./289
PP11,725 P 12/2000 Pieters ..... Plt./295

*Primary Examiner*—Kent Bell
*Assistant Examiner*—June Hwu
(74) *Attorney, Agent, or Firm*—Knobbe, Martens, Olson & Bear, LLP

(57) ABSTRACT

A new and distinct garden type chrysanthemum cultivar is disclosed, characterized by having a soft yellow daisy type inflorescence which naturally blooms in the middle of September. The plant habit of the new variety is exceptional in its round nature and extremely flexible habit.

1 Drawing Sheet

Figure 1:
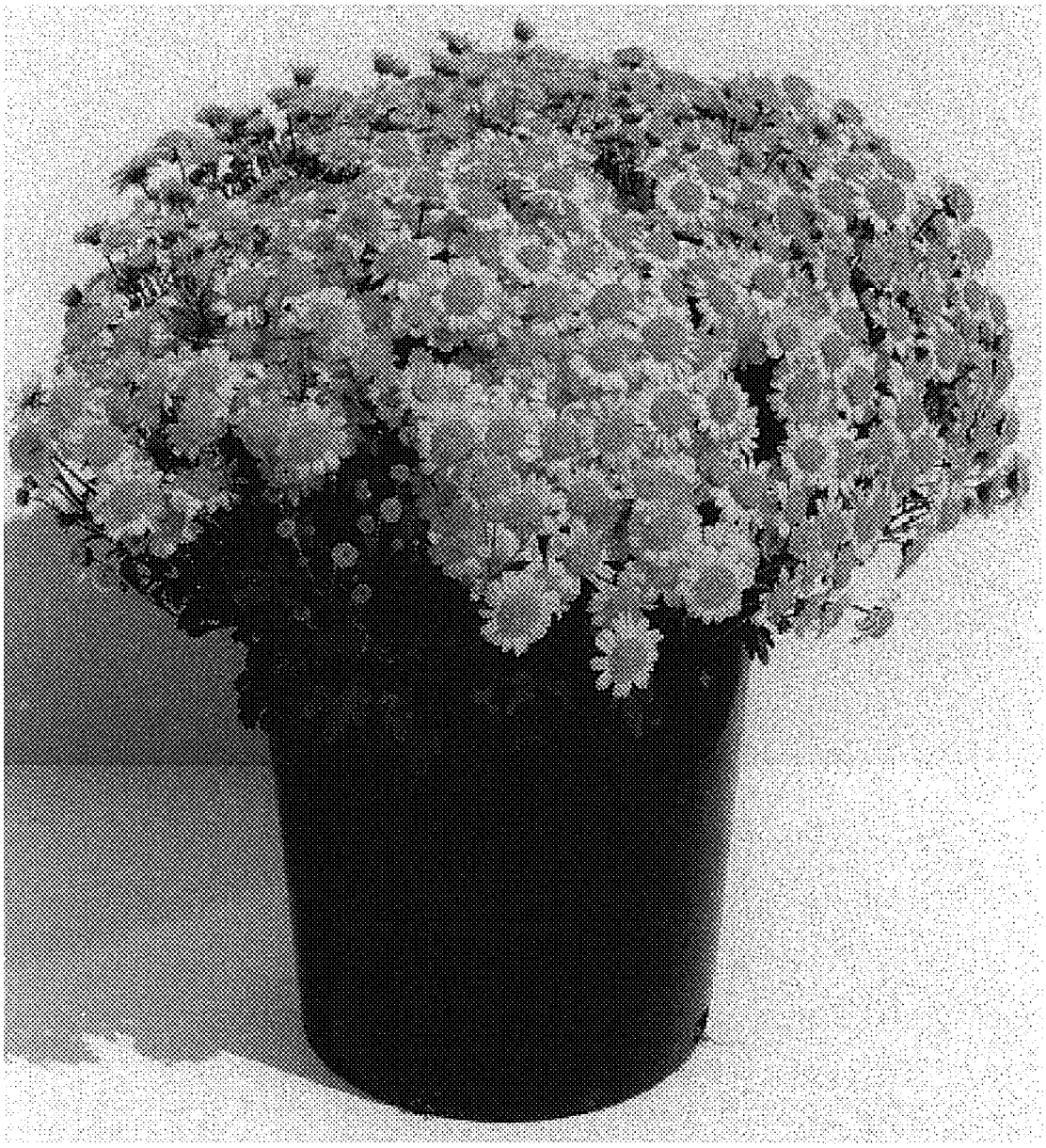

Latin name of the genus and species: *Chrysanthemum morifolium.*
Variety denomination: 'Gedi Two Ylbur'.

BACKGROUND OF THE INVENTION

The present invention relates to a new and distinct cultivar of garden-type Chrysanthemum plant, herein after referred to by the cultivar name 'Gedi Two Ylbur.' The new cultivar is a product of hybridization of a female parent Chrysanthemum plant variety 'Dark Veria' (U.S. Plant Pat. No. 10,215) and a male parent Chrysanthemum plant variety 'Gedi Two Ylnov' (U.S. Plant Pat. No. 14,414). The new cultivar was discovered and selected by Dirk Pieters in Oostnieuwkerke, Belgium, in September, 1999.

Asexual reproduction of the new cultivar by vegetative cuttings and tissue culture was performed in Staden, Belgium and in Oxnard, Calif., and has shown that the unique features of this cultivar are stable and reproduced true to type on successive generations.

SUMMARY OF THE INVENTION

The cultivar 'Gedi Two Ylbur' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Ylbur.' These characteristics in combination distinguish 'Gedi Two Ylbur' as a new and distinct Chrysanthemum cultivar:

1. Soft yellow daisy type inflorescence.
2. Naturally blooms in the middle of September.
3. Plant habit of the new variety is exceptional in its round nature.
4. The plant of the new variety has an extremely flexible habit.

Plants of the new cultivar are similar to plants of the female parent variety, 'Dark Veria' in most horticultural characteristics, however plants of the new cultivar have a larger diameter inflorescence than plants of the female parent variety. Further, the new variety blooms two weeks later than seed parent. Additionally, the new variety is a daisy-type chrysanthemum, while the seed parent 'Dark Veria' is a decorative-type chrysanthemum.

Plants of the new cultivar are similar to plants of the male parent variety, 'Gedi Two Ylnov' in most horticultural characteristics, however plants of the new cultivar have a daisy-type inflorescence while the male parent 'Gedi Two Ylnov' has a decorative-type inflorescence. Additionally, the new variety naturally blooms two weeks later than plants of 'Gedi Two Ylnov.' Further, the new variety has a more flexible plant habit than the male parent variety.

The new cultivar is similar to the commercial variety 'Gedi YT8' (U.S. Plant Pat. No. 11,725). In comparison to 'Gedi YT8', the new cultivar 'Gedi Two Ylbur' has a sturdier, longer lasting inflorescence which is smaller in diameter. Additionally, the new cultivar is taller and naturally blooms about 2 weeks earlier than 'Gedi YT8.'

BRIEF DESCRIPTION OF THE PHOTOGRAPH

The photograph shows a plant of 'Gedi Two Ylbur.' One cutting was planted in a two-gallon container in May. The plant was grown outdoors in Oxnard, Calif.

DETAILED BOTANICAL DESCRIPTION

In the following description, color references are made to The Royal Horticultural Society Colour Chart except where general terms of ordinary dictionary significance are used. The following observations and measurements describe 120 day old plants grown in Oxnard, Calif., during the month of September. Light conditions were bright, and no artificial shading was used. The humidity was low and no rainfall occurred. The growing temperature ranged from approximately 15° C. to 21° C. at night, and from approximately 19°

C. to 32° C., during the day. Measurements and numerical values represent averages of typical flowering types.

Botanical classification: *Chrysanthemum morifolium* cultivar 'Gedi Two Ylbur'.
Commercial classification: Garden-type Chrysanthemum.

PROPAGATION

Time to rooting: Approximately 7 to 14 days at approximately 21° C.
Root description: Fine, fibrous.

PLANT

Growth habit: Mounding herbaceous perennial.
Height: Approximately 24 cm.
Plant spread: Approximately 41 cm.
Growth rate: Moderate.
Branching characteristics: Free branching.
Length of lateral branches: Approximately 24.5 cm.
Internode length: Approximately 1.5 cm.
Number of leaves per lateral branch: Approximately 13.
Age of plant described: Approximately 120 days.

FOLIAGE

Leaf:
- *Arrangement.*—Alternate.
- *Average length.*—Approximately 3.3 cm.
- *Average width.*—Approximately 2 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near Green 139A. Young foliage under side: New Yellow-green 147A. Mature foliage upper side: Near Green 139A. Mature foliage under side: New Yellow-green 147A. Venation upper side: New Yellow-green 147C. Venation under side: New Yellow-green 147B.
- *Venation type.*—Net.

Petiole:
- *Average length.*—Approximately 1.3 cm.
- *Color.*—Near Green 139A.
- *Diameter.*—Approximately 2 mm.

BLOOM

Inflorescence:
- *Flowering habit.*—Induced by darkness period greater than approximately 13.5 hours, approximately 45 days of appropriate day length required to induce and develop blooms.
- *Inflorescence form.*—Daisy.
- *Disk diameter.*—Approximately 1.5 cm.
- *Flower fragrance.*—Not present.
- *Natural flowering season.*—Natural flowering begins between September 15 and September 22 in Southern Calif.
- *Number of inflorescences per lateral branch.*—Approximately 18.
- *Inflorescence diameter.*—Approximately 3.2 cm.
- *Inflorescence depth.*—Approximately 1 cm.
- *Inflorescence longevity on plant.*—Approximately 25 days.
- *Persistence.*—Persistent.

Ray florets:
- *Appearance.*—Matte.
- *Texture.*—Smooth.
- *Average number per flower.*—Approximately 27.
- *Shape.*—Oblong.
- *Aspect.*—Ridged.
- *Margin.*—Entire.
- *Apex.*—Retuse.
- *Length.*—Approximately 1.4 cm.
- *Width.*—Approximately 0.5 cm.
- *Color.*—Upper surface at first opening: Near Green-yellow 1A. Upper surface at maturity: Near Yellow 4B. Upper surface at fading: New Yellow 4C. Under surface at first opening: New Yellow 2B. Under surface at maturity: New Yellow 4C. Under surface at fading: New Yellow 4C.

Disc florets:
- *Appearance.*—Matte.
- *Texture.*—Smooth.
- *Average number per flower.*—Approximately 156.
- *Shape.*—Cylindric.
- *Apex.*—Obtuse.
- *Average length.*—Approximately 0.7 cm.
- *Average width.*—Approximately 1.5 mm.
- *Color.*—At first opening: New Yellow-green 151B. At maturity: Near Yellow 13A. At fading: Near Yellow 12A.

Peduncle:
- *Length.*—At terminal end (shortest): Approximately 5.4 cm. At lateral end (longest): Approximately 7.5 cm.
- *Angle to stem.*—Acute.
- *Strength.*—Moderate.
- *Color.*—New Yellow-green 146A.
- *Habit.*—Upright.
- *Diameter.*—Approximately 1.5 mm.
- *Texture.*—Lightly pubescent.

Inflorescence bud:
- *Length.*—Approximately 4 mm.
- *Diameter.*—Approximately 6 mm.
- *Form.*—Globular.
- *Color.*—New Yellow-green 144A.

Phyllaries (Involucral bracts):
- *Appearance.*—Matte.
- *Texture.*—Lightly pubescent.
- *Number.*—Approximately 29.
- *Shape.*—Oblanceolate.
- *Margin.*—Entire.
- *Apex.*—Acute.
- *Length.*—Approximately 6 mm.
- *Width.*—Approximately 3 mm.
- *Color.*—Upper side: Near Green 141A. Under side: Near Green 141A.

REPRODUCTIVE ORGANS

Ray florets:
- *Number of pistils per flower.*—1.
- *Stigma shape.*—2 branched.
- *Stigma color.*—Near Yellow 2B.
- *Style color.*—Near Yellow-green 154D.
- *Style length.*—Approximately 4 mm.
- *Stamens.*—Absent.

Disc florets:
- *Number of pistils per flower.*—1.
- *Stigma shape.*—2 branched.

*Stigma color.*—Near Yellow 2B.
*Style length.*—Approximately 4 mm.
*Style color.*—Near Yellow-green 154D.
*Number of stamens per flower.*—5.
*Anther shape.*—Tubular.
*Anther color.*—Near Yellow 12A.
*Pollen color.*—No pollen detected.

OTHER CHARACTERISTICS

Seed production: Commercially, this plant is not used or observed in a stage wherein seeds would be produced. Therefore, seed production has not been observed.

Disease resistance: Neither resistance nor susceptibility has been observed.

Drought tolerance and cold tolerance: Neither resistance nor susceptiblity has been observed.

What is claimed is:

1. A new and distinct cultivar of Chrysanthemum plant named 'Gedi Two Ylbur' as herein illustrated and described.

* * * * *